US012650365B1

(12) United States Patent
Bolton

(10) Patent No.: US 12,650,365 B1
(45) Date of Patent: Jun. 9, 2026

(54) METHOD AND APPARATUS FOR DNA SAMPLE COLLECTION FROM UNCOOPERATIVE SUSPECTS

(71) Applicant: John Darcy Bolton, Irvine, CA (US)

(72) Inventor: John Darcy Bolton, Irvine, CA (US)

(*) Notice: Subject to any disclaimer, the term of this patent is extended or adjusted under 35 U.S.C. 154(b) by 0 days.

(21) Appl. No.: 19/334,920

(22) Filed: Sep. 21, 2025

Related U.S. Application Data

(63) Continuation-in-part of application No. 18/597,994, filed on Mar. 7, 2024.

(60) Provisional application No. 63/630,313, filed on Jan. 23, 2024.

(51) Int. Cl.
| | |
|---|---|
| *E03D 9/00* | (2006.01) |
| *G01N 1/20* | (2006.01) |
| *G01N 33/487* | (2006.01) |

(52) U.S. Cl.
CPC ............ *G01N 1/2035* (2013.01); *E03D 9/00* (2013.01); *G01N 33/4875* (2013.01); *G01N 2001/2071* (2013.01)

(58) Field of Classification Search
CPC ............ G01N 1/2035; G01N 33/4875; G01N 2001/2071; E03D 9/00
See application file for complete search history.

(56) References Cited

U.S. PATENT DOCUMENTS

| | | | | |
|---|---|---|---|---|
| 9,766,257 | B1* | 9/2017 | Hall ........................ | G01N 33/94 |
| 2003/0149408 | A1* | 8/2003 | Levinson ............. | A61B 10/007 604/329 |

| | | | | |
|---|---|---|---|---|
| 2008/0168597 | A1* | 7/2008 | Bartlett ................... | E03D 11/11 4/321 |
| 2014/0165279 | A1* | 6/2014 | Plugovoy ................. | E03D 9/04 4/348 |
| 2015/0013058 | A1* | 1/2015 | Bucher ................... | E03D 9/037 4/224 |
| 2016/0201312 | A1* | 7/2016 | Akar ........................ | E03D 7/00 4/417 |
| 2018/0080855 | A1* | 3/2018 | Taylor .................. | G01N 1/2813 |
| 2019/0062813 | A1* | 2/2019 | Amin .................... | B01L 3/5635 |
| 2019/0320650 | A1* | 10/2019 | Johnson ................. | A01N 1/145 |

(Continued)

OTHER PUBLICATIONS

Thermal Custom Packaging Maintains Proper Preservation of Law Enforcement Evidence with PC-21 Phase Change Material Case PR Newswire, Apr. 12, 2022 (Year: 2022) (Year: 2022).*

*Primary Examiner* — Catherine T. Rastovski
*Assistant Examiner* — Sharad Timilsina
(74) *Attorney, Agent, or Firm* — Gugliotta & Gugliotta LPA

(57) ABSTRACT

A method and apparatus for collecting DNA samples from uncooperative suspects are provided. A modified bathroom fixture, including a toilet with an empty reservoir tank and a missing handle on the water fill valve, retains excreted material in the toilet bowl, allowing for easy collection of DNA samples. In an alternate embodiment, the toilet's reservoir tank is full, and the water fill valve is in the on position, but the waste flush is diverted to a holding tank. This enables DNA technicians to collect samples from the excreted material for forensic analysis. The invention eliminates the need for costly and time-consuming stakeouts, provides a quick and reliable method for DNA sample collection, reduces the risk of contamination, and allows for immediate sample collection, advancing forensic DNA analysis.

13 Claims, 2 Drawing Sheets

(56)         References Cited

U.S. PATENT DOCUMENTS

2021/0245941 A1*   8/2021   Crawley ................ B65D 55/14
2023/0399148 A1*  12/2023   Wadekar ........... B65D 41/0492

* cited by examiner

METHOD AND APPARATUS FOR DNA SAMPLE COLLECTION FROM UNCOOPERATIVE SUSPECTS

RELATED APPLICATIONS

The present invention is a Continuation in Part of U.S. Ser. No. 18/597,994, filed on Mar. 7, 2024, which claimed benefit of U.S. Provisional Application Ser. No. 63/630,313, filed on Jan. 22, 2024. All Related Applications are incorporated by reference as is fully rewritten herein.

BACKGROUND OF THE INVENTION

1. Field of the Invention

The present invention relates generally DNA sample collection from uncooperative suspects and, more particularly, to a modified bathroom fixture designed to facilitate the collection of DNA from uncooperative suspects by retaining their excretions in the toilet bowl, thereby eliminating the need for costly and time-consuming stakeouts.

2. Description of the Related Art

It was discovered in 1986 that every human has chromosomes that are made up of a chemical widely known as DNA. Every person has a unique pattern of DNA Since DNA is different in each human a positive identification may be made of any individual from his DNA.

Police were quick to realize that analysis of a person's DNA was a very useful forensic tool. Suspects are also well aware of the potential identification of a perpetrator of a crime and frequently they refuse to give a DNA sample.

When an uncooperative suspect refuses to give a specimen of his DNA the police are forced to do a stakeout. Usually, two officers are stationed near the accused's workplace or home. They sit there, waiting for the suspect to expectorate or drop a paper cup he used to drink from in a trash container. When they see that they go over and collect the spittle off the road or the drink container from the trash bin.

The challenge is that it is prohibitively expensive to have two officers sitting out for days or even weeks in the hope of getting a DNA sample. After that huge expenditure of time and money they may see nothing and collect nothing, or they may collect a specimen that turns out to be useless because the officer pulled the wrong drink cup out of the trash can or there was contamination on the road that destroyed the specimen.

Another problem is that it can cause an extremely long delay before DNA is obtained and a suspect identified. During the delay the criminal remains free and able to continue his illegal activity.

A urine hat is a type of toilet insert that is known and used in medical environments to capture urine for measurement and analysis. Essentially, a urine hat is a large plastic measuring cup that sits on the rim of a toilet bowl and collects urine while the patient uses the toilet in a normal fashion. Following a urinary event, a nurse enters the patient's room, documents the level of urine in the hat, empties the contents into the toilet bowl and then flushes the toilet.

However, such a collection device would be ineffective without the cooperation of the user providing the sample.

Consequently, a need exists for an improved, cost effective and manpower efficient way of collecting DNA in such scenarios.

SUMMARY OF THE INVENTION

It is thus an object of the present invention to alleviate difficulties caused to law enforcement in the collection and obtaining DNA samples from uncooperative suspects.

It is a feature of the present invention to provide a modified bathroom fixture, a toilet, to facilitate the collection of DNA from a suspect who is unwilling to provide a sample.

The present invention provides for a modified bathroom for use in law enforcement situations where an uncooperative suspect refuses to provide a DNA sample. The modified bathroom has a toilet with an empty reservoir tank and a missing flush handle (or other external flushing mechanism), thereby preventing flushing by the suspect. When the suspect uses the bathroom, the excreted material remains in the toilet bowl. In an alternate embodiment, the reservoir tank is full, and the fill valve is in the on position, but the waste is diverted to a holding tank. DNA technicians can then collect samples from the excreted material, which contains the suspect's DNA, for forensic analysis.

By emptying the reservoir tank and removing the handle of the water fill valve, the invention ensures that the excreted material remains in the toilet bowl, allowing for easy collection by DNA technicians. This modification eliminates the need for costly and time-consuming stakeouts, provides a quick and reliable method for DNA collection, and reduces the risk of contamination, making it a significant advancement in forensic DNA analysis.

This method eliminates the need for costly and time-consuming stakeouts and reduces the risk of contamination, ensuring a quick and reliable DNA sample collection process.

It is an advantage of the present invention that it eliminates the need for costly and time-consuming stakeouts to collect DNA from uncooperative suspects.

It is another advantage of the present invention that it provides a quick and reliable method for DNA sample collection.

It is another advantage of the present invention that it reduces the risk of contamination, ensuring the reliability of DNA samples.

It is another advantage of the present invention that it allows for the immediate collection of DNA samples, avoiding long delays in the identification and apprehension of suspects.

It is another advantage of the present invention that it is a cost-effective solution for law enforcement agencies.

Further objects, features, elements and advantages of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Figure 1:
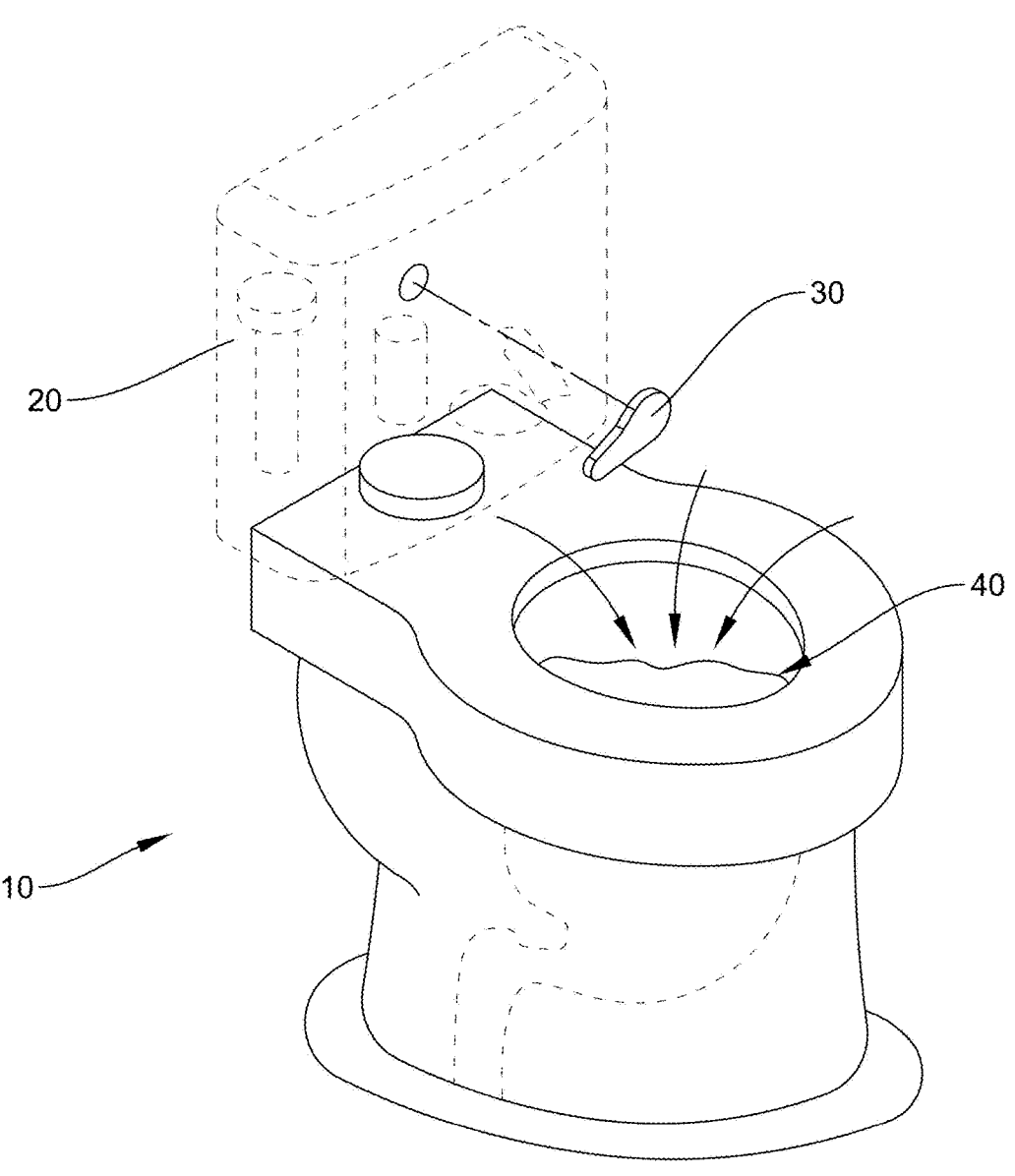
FIG. 1 is a schematic diagram of a specimen collection toilet according to a preferred embodiment of the present invention.

The best mode for carrying out the invention is presented in terms of its preferred embodiment, herein depicted within the Figures. It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims. Finally, unless a claim element is defined by reciting the word "means" and a function without the recital of any structure, it is not intended that the scope of any claim element be interpreted based on the application of 35 U.S.C. § 112(f).

The best mode for carrying out the invention is presented in terms of its preferred embodiment, herein depicted within the Figures.

1. Detailed Description of the Figures

Referring now to the drawings, wherein like reference numerals indicate the same parts throughout the several views, a method for collecting DNA sample from uncooperative suspects is described, generally, according to the preferred embodiment of the present invention. A modified toilet 10 is provided having no reservoir tank 20 or, optionally, an empty reservoir tank 20. A flush handle or functionally equivalent external flushing mechanism 30 is missing or removable handle, preventing flushing and ensuring that the excreted material remains in the toilet bowl 40 after use. In a first alternate configuration, the handle 30 may be provided configured to be removable and may be reattached, after specimen collection, for flushing of the toilet.

Figure 2:
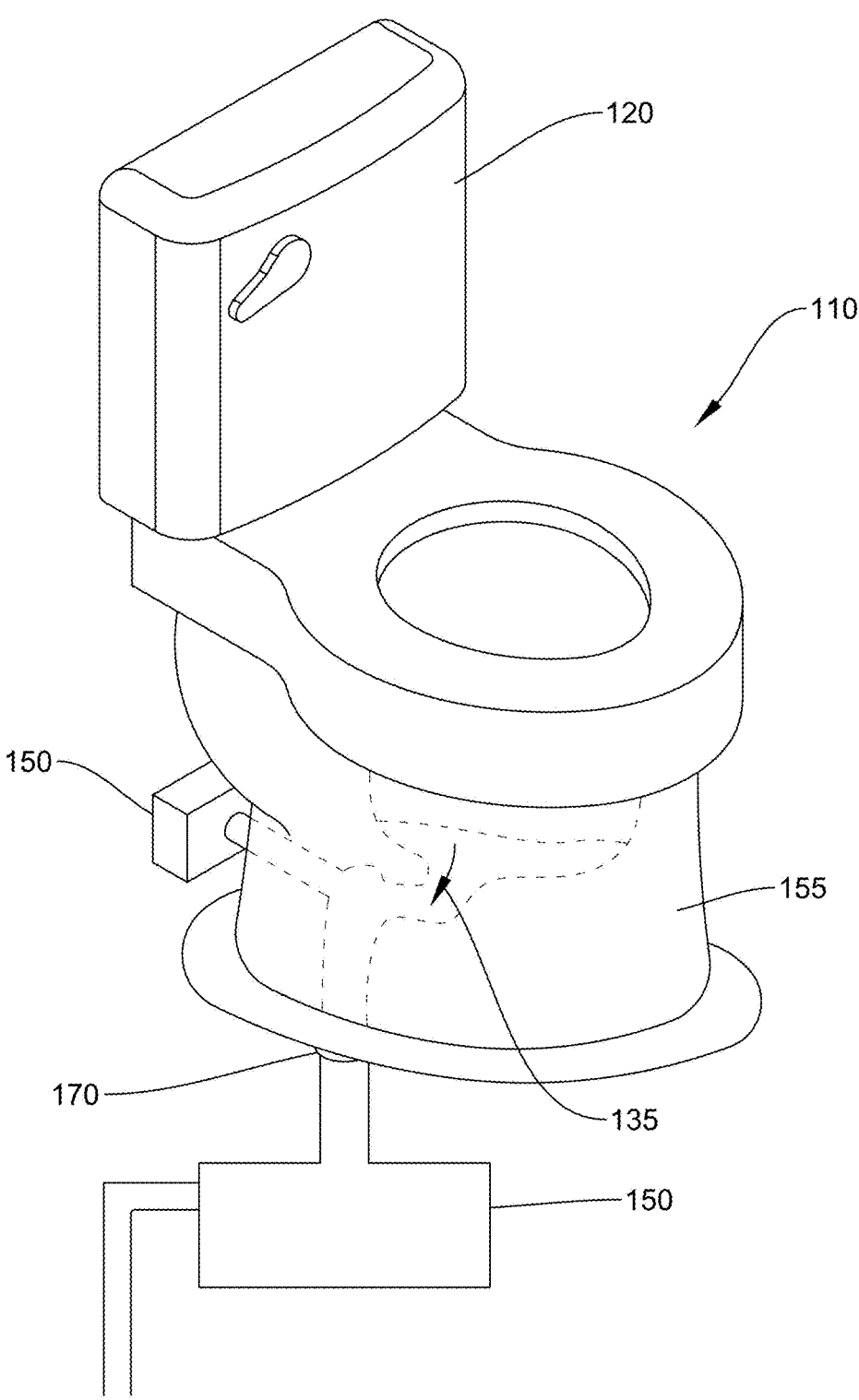
FIG. 2 is a schematic diagram of a toilet with a collection sample reservoir, including a diversion conduit 135, holding tank 150, and a biometric lock or switch 160 on the holding tank.

In an alternate embodiment, a toilet 110 may be provided having a full reservoir tank 120 and an on-position water fill valve, but with the waste flush 135 diverted to a holding tank 150. The holding tank 150 is equipped with a tamper-evident seal and a biometric locking mechanism requiring authorized forensic personnel to authenticate their identity (e.g., via fingerprint or retinal scan) before accessing the contents. As shown in FIG. 2, the holding tank 150 includes a biometric lock 160 (e.g., fingerprint scanner) to restrict access. The holding tank 150 may be integrated with or adjacent to the toilet pedestal 155 or, alternately, provided below the floor flange 170 for retention within the plumbing system below a floor. After a suspect uses the toilet, the waste flush is diverted to the holding tank 150, sealed with a tamper-evident band displaying a unique identification code, and prepared for secure transport to a forensic laboratory. In some embodiments, the water fill valve may include a locking mechanism, such as a key-operated or biometric switch, to secure it in the on position (allowing tank refilling) or off position (preventing refilling). This lock is accessible only to authorized personnel, ensuring the valve remains in the desired configuration during suspect use and sample collection. In either configuration, the retention of a flush discharge sample allows DNA technicians to easily collect samples from the excreted material, which contains the suspect's DNA.

In conjunction with any modified toilet configuration, a method of specimen collection according to the present invention eliminates the need for costly and time-consuming stakeouts, provides a quick and reliable DNA sample collection process, and reduces the risk of contamination. After the suspect uses the toilet, the excreted material is retained in the toilet bowl 40 or diverted to the holding tank 150. Authorized personnel then access the holding tank 150 using the biometric lock, apply a tamper-evident seal, and transport the sealed tank or its contents in a secure transport container to a forensic laboratory. The secure transport container may be temperature-controlled (e.g., refrigerated between 2-8° C.) to prevent DNA degradation during transit. This process ensures chain-of-custody integrity and preserves DNA sample viability, making it a significant advancement in forensic DNA analysis.

2. Operation of the Preferred Embodiment

The present invention provides a method for collecting DNA samples from uncooperative suspects using a modified bathroom fixture. In operation, when a suspect is brought to a police station for an interview and requests a bathroom break, they are directed to the modified bathroom or modified toilet. The modified toilet in the bathroom has an empty reservoir tank and a missing flush handle on the water fill valve, preventing flushing and ensuring that the excreted material remains in the toilet bowl after use. Alternatively, in an alternate embodiment, the toilet may have a full reservoir tank and an on-position water fill valve, but with the waste flush diverted to a holding tank. This allows DNA technicians to easily collect samples from the excreted material, which contains the suspect's DNA. This method eliminates the need for costly and time-consuming stakeouts, provides a quick and reliable DNA sample collection process, and reduces the risk of contamination, making it a significant advancement in forensic DNA analysis.

For a variety of reasons the DNA technician may desire to collect and hold the excreted sample. For example, the technician may want to be sure the DNA test is working properly and giving reliable results before they discard the DNA sample. They may want to retain the DNA sample to be able to take a second sample in case the first sample is lost or contaminated.

In the alternative embodiment, the apparatus is a bathroom as described above, but the toilet tank reservoir is full of water, and the tank water fill valve is in the on position. The toilet may be flushed in the ordinary way, with the difference being that the waste flush does not empty into the municipal sewer system but into an alternative waste pipe leading to a holding tank 150. The holding tank 150 is fitted with a tamper-evident seal and a biometric locking mechanism to prevent unauthorized access, ensuring that only trained forensic personnel can retrieve the sample. After sealing, the tank or its contents are transported in a temperature-controlled secure container to maintain DNA integrity during transit to a forensic laboratory.

In some embodiments, the water fill valve may include a locking mechanism, such as a key-operated or biometric switch, to secure it in the on position (allowing tank refilling) or off position (preventing refilling). This lock is accessible only to authorized personnel, ensuring the valve remains in the desired configuration during suspect use and sample collection.

In any embodiment, both urine and stool are rich in human cells filled with the suspect's unique DNA (deoxyribonucleic acid). The technician uses a forensic DNA collection kit, comprising sterile cotton-tipped swabs, preservation solutions (e.g., buffered saline), and tamper-evident packaging, to recover an adequate sample. The forensic DNA collection kit may include sterile cotton-tipped swabs for sample recovery, preservation solutions such as buffered saline to maintain DNA viability, and tamper-evident packaging bags or tubes marked with unique codes for secure storage and transport. The technician needs only swish a cotton-tipped stick around in the liquid in the toilet bowl or holding tank to collect a sample. If there is solid waste, touching the solid waste with a tipped stick will yield a rich harvest of cells containing DNA. The collected sample is then sealed in tamper-evident packaging marked with a unique identification code for chain-of-custody tracking and placed in a temperature-controlled compartment to preserve DNA integrity until analysis.

The foregoing descriptions of specific embodiments of the present invention are presented for purposes of illustration and description. To enhance security and reliability, the modified toilet system may include a biometric locking mechanism on the holding tank 150 or toilet components, ensuring that only authorized personnel can access the sample post-collection. The tamper-evident seals and unique identification codes applied to the holding tank or packaging provide verifiable evidence of an intact chain of custody, while the temperature-controlled transport container prevents degradation of the DNA sample during transit to a forensic laboratory. These features collectively advance the invention's utility in forensic DNA analysis.

The foregoing descriptions of specific embodiments of the present invention are presented for purposes of illustration and description. The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples, and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of Warner-Jenkinson Company, v. Hilton Davis Chemical, 520 US 17 (1997) or Festo Corp. v. Shoketsu Kinzoku Kogyo Kabushiki Co., 535 U.S. 722 (2002), or other similar caselaw or subsequent precedent should not be made if any future claims are added or amended subsequent to this Patent Application.

What is claimed is:

1. A method for collecting DNA samples from uncooperative suspects in a law enforcement setting, comprising:
   providing a modified toilet having an excrement retention means for retaining a suspect's urine and/or feces, wherein the excrement retention means comprises:
   a toilet bowl configured to retain excreted material;
   a diversion conduit in fluid communication between the toilet bowl and a holding tank; and
   a biometric locking mechanism on the holding tank accessible only to authorized forensic personnel;
   directing the suspect to use the modified toilet while in custody;
   allowing the suspect to excrete into the toilet bowl;
   diverting a waste flush from the toilet bowl to the secure holding tank;
   sealing the secure holding tank with a tamper-evident seal bearing a unique identification code; and
   collecting DNA samples from the excreted material in the secure holding tank using the forensic DNA collection kit comprising sterile tools and preservation solutions" to the collecting step for better support.

2. The method of claim 1, wherein the modified toilet further comprises:
   a reservoir tank that is empty and a missing flush handle, preventing the suspect from flushing the toilet, thereby retaining the excreted material in the toilet bowl for immediate collection.

3. The method of claim 1, wherein the modified toilet further comprises:
   a full reservoir tank and a water fill valve in an on position, allowing the suspect to flush the toilet, with the waste flush being diverted to the secure holding tank via the diversion conduit.

4. The method of claim 1, further comprising:
   transporting the sealed holding tank or its contents to a forensic laboratory in a temperature-controlled secure transport container to preserve DNA integrity during transit.

5. A modified bathroom fixture for collecting DNA samples from uncooperative suspects, comprising:
   an excrement retention means for retaining a suspect's urine and/or feces, wherein the excrement retention means comprises:
   a tankless toilet bowl, or a toilet bowl with a closed and lockable tank, and a removable flush handle configured to be operable only by authorized personnel; and
   a biometric locking mechanism on the holding tank accessible only to authorized forensic personnel;
   a diversion conduit in fluid communication between the toilet bowl and a holding tank, wherein the holding tank is accessible only to authorized forensic personnel;
   diverting a waste flush from the toilet to the holding tank;
   sealing the holding tank to prevent tampering; and
   transporting the sealed holding tank to a forensic laboratory for DNA sample collection and analysis.

6. The modified bathroom fixture of claim 5, wherein the toilet further comprises:

an empty reservoir tank and a missing flush handle, preventing flushing by the suspect and retaining the excreted material in the toilet bowl.

7. The modified bathroom fixture of claim 6, further comprising:

a water fill valve in an on position and configured to be locked in the on position or in an off position to allow authorized personnel to flush the toilet after forensic sample collection, with the waste flush being diverted to the secure holding tank.

8. The modified bathroom fixture of claim 5, wherein the tamper-evident seal includes a unique identification code for chain-of-custody tracking.

9. The modified bathroom fixture of claim 8, further comprising a forensic DNA collection kit comprising sterile collection tools, preservation solutions, and tamper-evident packaging.

10. A system for collecting DNA samples from uncooperative suspects in a law enforcement context, comprising:

a modified bathroom fixture including:

a toilet having a toilet bowl, a diversion conduit, and a secure holding tank configured to retain a suspect's excreted material;

a biometric locking mechanism on the holding tank accessible only to authorized forensic personnel; and a tamper-evident seal with a unique identification code for securing the holding tank after use;

a forensic DNA collection kit comprising sterile cotton-tipped swabs, preservation solutions, and tamper-evident packaging for collecting and preserving DNA samples from the excreted material; and a temperature-controlled secure transport container for transferring the collected DNA samples to a forensic laboratory while maintaining DNA integrity.

11. The system of claim 10, wherein the toilet further comprises:

an empty reservoir tank and a missing flush handle, preventing the suspect from flushing the toilet and retaining the excreted material in the toilet bowl.

12. The system of claim 10, wherein the toilet further comprises:

a full reservoir tank and a water fill valve in an on position, allowing the suspect to flush the toilet, with the waste flush being diverted to the holding tank.

13. The system of claim 10, wherein the holding tank includes a temperature-controlled compartment to preserve the DNA integrity of the excreted material prior to collection.

* * * * *